(12) United States Patent
Carlson et al.

(10) Patent No.: US 7,248,919 B2
(45) Date of Patent: *Jul. 24, 2007

(54) CARDIAC RHYTHM MANAGEMENT SYSTEM USING TIME-DOMAIN HEART RATE VARIABILITY INDICIA

(75) Inventors: Gerrard M. Carlson, Champlin, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 612 days.

This patent is subject to a terminal disclaimer.

(21) Appl. No.: 10/726,062

(22) Filed: Dec. 2, 2003

(65) Prior Publication Data

US 2004/0193066 A1    Sep. 30, 2004

Related U.S. Application Data

(63) Continuation of application No. 09/802,316, filed on Mar. 8, 2001, now Pat. No. 6,678,547.

(51) Int. Cl.
*A61N 1/365* (2006.01)
(52) U.S. Cl. ......................................... 607/4
(58) Field of Classification Search ................ 600/508, 600/509, 513–518, 521; 607/4, 5, 9, 14
See application file for complete search history.

(56) References Cited

U.S. PATENT DOCUMENTS

| | | | |
|---|---|---|---|
| 5,291,400 A | 3/1994 | Gilham | 364/413.06 |
| 5,466,245 A | 11/1995 | Spinelli et al. | 607/17 |
| 5,560,370 A | 10/1996 | Verrier et al. | 128/705 |
| 5,603,331 A | 2/1997 | Heemels et al. | 128/696 |
| 5,645,570 A | 7/1997 | Corbucci | 607/5 |
| 5,682,901 A | 11/1997 | Kamen | 128/706 |
| 5,749,900 A | 5/1998 | Schroeppel et al. | |
| 5,755,671 A | 5/1998 | Albrecht et al. | 600/516 |
| 5,842,997 A | 12/1998 | Verrier et al. | 600/518 |
| 5,891,044 A | 4/1999 | Golosarsky et al. | 600/509 |

(Continued)

FOREIGN PATENT DOCUMENTS

EP    0709112    5/1996

(Continued)

OTHER PUBLICATIONS

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology; published by the American Heart Association, Inc.; European Society of Cardiology,(1996),pp. 354-381.

(Continued)

*Primary Examiner*—George R. Evanisko
(74) *Attorney, Agent, or Firm*—Schwegman, Lundberg, Woessner & Kluth, P.A.

(57) ABSTRACT

A cardiac rhythm management system that provides an indication of patient well-being based on the autonomic balance between the sympathetic and parasympathetic/vagal components of the autonomic nervous system, using time-domain processing of frequency components of a heart rate interval signal.

22 Claims, 9 Drawing Sheets

U.S. PATENT DOCUMENTS

| | | | |
|---|---|---|---|
| 5,893,882 | A | 4/1999 | Peterson et al. .............. 607/14 |
| 5,921,940 | A | 7/1999 | Verrier et al. ............... 600/518 |
| 5,941,831 | A | 8/1999 | Turcott ....................... 600/515 |
| 6,021,351 | A | 2/2000 | Kadhiresan et al. .......... 607/19 |
| 6,026,320 | A | 2/2000 | Carlson et al. ............. 600/510 |
| 6,035,233 | A | 3/2000 | Schroeppel et al. ........ 600/515 |
| 6,042,548 | A | 3/2000 | Giuffre ....................... 600/483 |
| 6,135,970 | A | 10/2000 | Kadhiresan et al. ........ 600/595 |
| 6,144,878 | A | 11/2000 | Schroeppel et al. ........ 600/515 |
| 6,216,032 | B1 | 4/2001 | Griffin et al. ............... 600/515 |
| 6,224,553 | B1 | 5/2001 | Nevo ........................ 600/437 |
| 6,246,909 | B1 | 6/2001 | Ekwall .......................... 607/9 |
| 6,253,107 | B1 | 6/2001 | Albrecht et al. |
| 6,269,263 | B1 | 7/2001 | Ohnishi et al. ............. 600/518 |
| 6,301,499 | B1 | 10/2001 | Carlson et al. |
| 6,314,321 | B1 | 11/2001 | Morris |
| 6,358,201 | B1 | 3/2002 | Childre et al. .............. 600/300 |
| 6,390,986 | B1 | 5/2002 | Curcie et al. ............... 600/485 |
| 6,480,733 | B1 | 11/2002 | Turcott ....................... 600/516 |
| 6,529,772 | B2 | 3/2003 | Carlson et al. |
| 6,678,547 | B2 * | 1/2004 | Carlson et al. ............. 600/515 |
| 7,062,314 | B2 * | 6/2006 | Zhu et al. ................... 600/515 |
| 2002/0029000 | A1 | 3/2002 | Ohsaki |
| 2002/0068875 | A1 | 6/2002 | Schroeppel et al. |
| 2002/0072683 | A1 | 6/2002 | Schroeppel et al. ........ 600/515 |
| 2006/0161208 | A1 | 7/2006 | Pastore et al. |
| 2006/0161209 | A1 | 7/2006 | Pastore et al. |
| 2006/0161210 | A1 | 7/2006 | Pastore et al. |

FOREIGN PATENT DOCUMENTS

| | | |
|---|---|---|
| WO | WO-94/06350 | 3/1994 |
| WO | WO-98/15319 | 4/1998 |
| WO | WO-00/04950 | 2/2000 |
| WO | WO-00/38782 | 7/2000 |
| WO | WO-00/44274 | 8/2000 |
| WO | WO-00/51680 | 9/2000 |

OTHER PUBLICATIONS

"Heart Rate Variability: Standards of Measurement, Physiological Interpretation, and Clinical Use", *Circulation*, 93, (1996),pp. 1043-1065.

Behrens, S., et al., "Effects of Amiodarone on the Circadian Pattern of Sudden Cardiac Death (Departrment of Vererans Affairs Congestive Heart Failure-Survival Trial of Antiarrhythmic Therapy)", *Am. J. Cardiol.*, 80, (Jul. 1997),pp. 45-48.

Behrens, S., et al., "Modification of the Circadian Pattern of Ventricular Tachyarrhythmias by Beta-Blocker Therapy", *Clin. Cardiol.*, 20, (1997),pp. 253-257.

Berger, R. D., et al., "An Efficient Algorithm for Spectral Analysis of Heart Rate Variability", *IEEE Transactions on Biomedical Engineering*, BME-33 (9), (Sep. 1986),pp. 900-904.

Bigger, J. T., "Correlations Among Time and Frequency Domain Measures of Heart Period Variability Two Weeks After Acute Myocardial Infarction", *Arrhythmias and Conduction Disturbances*, 69, (Apr. 1, 1992),pp. 891-898.

Bigger, Jr., J. T., "Spectral Analysis of R-R Variability to Evaluate Autonomic Physiology and Pharmacology and to Predict Cardiovascular Outcomes in Humans", *Am. J. Cardiol.*, 69, (1992),pp. 891-898.

Bocker, D., et al., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract)*, Barcelona, Spain,(Jun. 11, 2001), 1 p.

Crawford, Michael H., et al., "ACC/AHA Guidelines for Ambulatory Electrocardiography", *JACC* vol. 34, No. 3, Published by Elsevier Science Inc.,(Sep. 1999),912-948.

Hayano, J., et al. "Circadian Rhythms of Atrioventricular Conduction Properties in Chronic Atrial Fibrillation With and Without Heart Failure", *JACC*, 31 (1), (Jan. 1998),pp. 158-166.

Lavery, C. E., et al., "Nonuniform Nighttime Distribution of Acute Cardiac Events", *Circulation*, 96 (10), (Nov. 18, 1997),pp. 3321-3327.

Peckova, M., et al., "Circadian Variations in the Occurence of Cardiac Arrests", *Circulation*, 98 (1), (1998),pp. 31-39.

Yamashita, T., et al., "Circadian Variation of Paroxysmal Atrial Fibrillation", *Circulation*, 96 (5), (Sep. 2, 1997),pp. 1537-1541.

Abildstrom, S. Z., et al., "Heart rate versus heart rate variability in risk prediction after myocardial infarction", *J Cardiovasc Electrophysiol.*, 14(2), (Feb. 2003), 168-73.

Bigger, J. T., et al., "Frequency domain measures of heart period variability to assess risk late after myocardial infarction.", *J Am Coll Cardiol.*, 21(3), (Mar. 1, 1993),729-36.

Tran, Thong, et al., "Accuracy of Ultra-Short Heart Rate Variability Measures", *EMBC*, (2003),2424-2427.

\* cited by examiner

CARDIAC RHYTHM MANAGEMENT SYSTEM USING TIME-DOMAIN HEART RATE VARIABILITY INDICIA

RELATED APPLICATIONS

This application is a continuation of U.S. patent application Ser. No. 09/802,316, filed on Mar. 8, 2001, now issued as U.S. Pat. No. 6,678,547, the specification of which is incorporated herein by reference.

TECHNICAL FIELD

The present system relates generally to cardiac rhythm management systems and particularly, but not by way of limitation, to such a system using time-domain heart rate variability indicia.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency. Cardiac rhythm management systems also include coordination devices for coordinating the contractions of both the right and left sides of the heart for improved pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by physicians treating cardiovascular patients is assessing patient well-being for providing a prognosis or for adjusting therapy to improve the patient's prognosis. Heart rate variability ("HRV") is thought to provide one such assessment of cardiovascular health. The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system.

The autonomic nervous system itself has two components: sympathetic and parasympathetic (or vagal). The sympathetic component of the autonomic nervous system is relatively slow acting, and is associated with a tendency to raise heart rate, blood pressure, and/or cardiac output. The parasympathetic/vagal component of the autonomic nervous system, which provides a relatively faster response than the sympathetic component, is associated with a tendency to reduce heart rate, blood pressure, and/or cardiac output. A proper balance between the sympathetic and parasympathetic components of the autonomic nervous system is important. Therefore, an indication of this balance of the components of the autonomic nervous system, which is sometimes referred to as "autonomic balance," "sympathetic tone," or "sympathovagal balance," provides a useful indication of the patient's well-being.

One technique for providing an indication of the balance of the components of the autonomic nervous system is provided by the beat-to-beat heart rate variability, as discussed above. More particularly, intrinsic ventricular contractions are detected. The time intervals between these contractions, referred to as the R—R intervals, are recorded after filtering out any ectopic contractions, that is, ventricular contractions that are not the result of a normal sinus rhythm. This signal of R—R intervals is typically transformed into the frequency-domain, such as by using fast Fourier transform ("FFT") techniques, so that its spectral frequency components can be analyzed. Two frequency bands are of particular interest: a low frequency (LF) band in the frequency ("f") range $0.04~\text{Hz} \leq f < 0.15~\text{Hz}$, and a high frequency (HF) band in the frequency range $0.15~\text{Hz} \leq f \leq 0.40~\text{Hz}$. The HF band of the R—R interval signal is influenced only by the parasympathetic/vagal component of the autonomic nervous system. The LF band of the R—R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health.

Such spectral analysis of the frequency components of the R—R interval signal has required an FFT (or other parametric transformation, such as autoregression) transformation from the time domain into the frequency domain. Implantable cardiac rhythm management devices, however, typically do not presently have the dedicated hardware to perform such FFT transformations. Even if an implantable cardiac rhythm management device did have such dedicated FFT hardware, performing the transformation would be computationally expensive, requiring increased power consumption, and shortening time during which the implanted battery-powered device can be used before its replacement is required. Therefore, there is a need to provide such an indication of patient well-being without requiring a computationally expensive transformation of the R—R interval signal into the frequency domain.

SUMMARY

This document describes a cardiac rhythm management system that provides an indication of patient well-being based on the autonomic balance between the sympathetic and vagal components of the autonomic nervous system, using time-domain processing of frequency components of a heart rate variability signal.

In one embodiment, the cardiac rhythm management system provides a method that detects heart contractions over a time period. A time-domain first signal represents time intervals between the detected heart contractions. The first signal is filtered to obtain a time-domain second signal including frequency components substantially in a first frequency band. The first signal is also filtered to obtain a time-domain third signal including frequency components substantially in a second frequency band that is different from the first frequency band. Based on the second and third signals, the system provides an indication associated with an autonomic nervous system.

In another embodiment, the cardiac rhythm management system provides a method that detects contractions of a heart over a time period. A time-domain first signal represents time intervals between the detected heart contractions. The first signal is filtered to obtain a time-domain second signal having frequency components substantially in a first frequency band. The system provides a substantially real-time time-domain indication, based on the second signal, of a balance between a sympathetic and a parasympathetic/vagal components of an autonomic nervous system. In a further embodiment, the system delivers therapy to a heart based on this indication of autonomic balance.

In another embodiment, the cardiac rhythm management system includes a heart contraction detection module, providing a heart rate interval signal carrying information regarding intervals between heart contractions. A bandpass filter is coupled to the detection module for receiving the heart rate interval signal. The bandpass filter provides a time-domain bandpass filtered signal output. A variance module is coupled to the bandpass filter for receiving the bandpass filtered signal. The variance modules provides a resulting variance signal. An autonomic balance indicator module is coupled to the variance module, and provides an indication of a balance between sympathetic and parasympathetic components of an autonomic nervous system, based on the variance signal. In a further embodiment, a therapy module, which is adapted to be coupled to a heart, provides therapy to the heart based at least in part on the autonomic balance indication. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
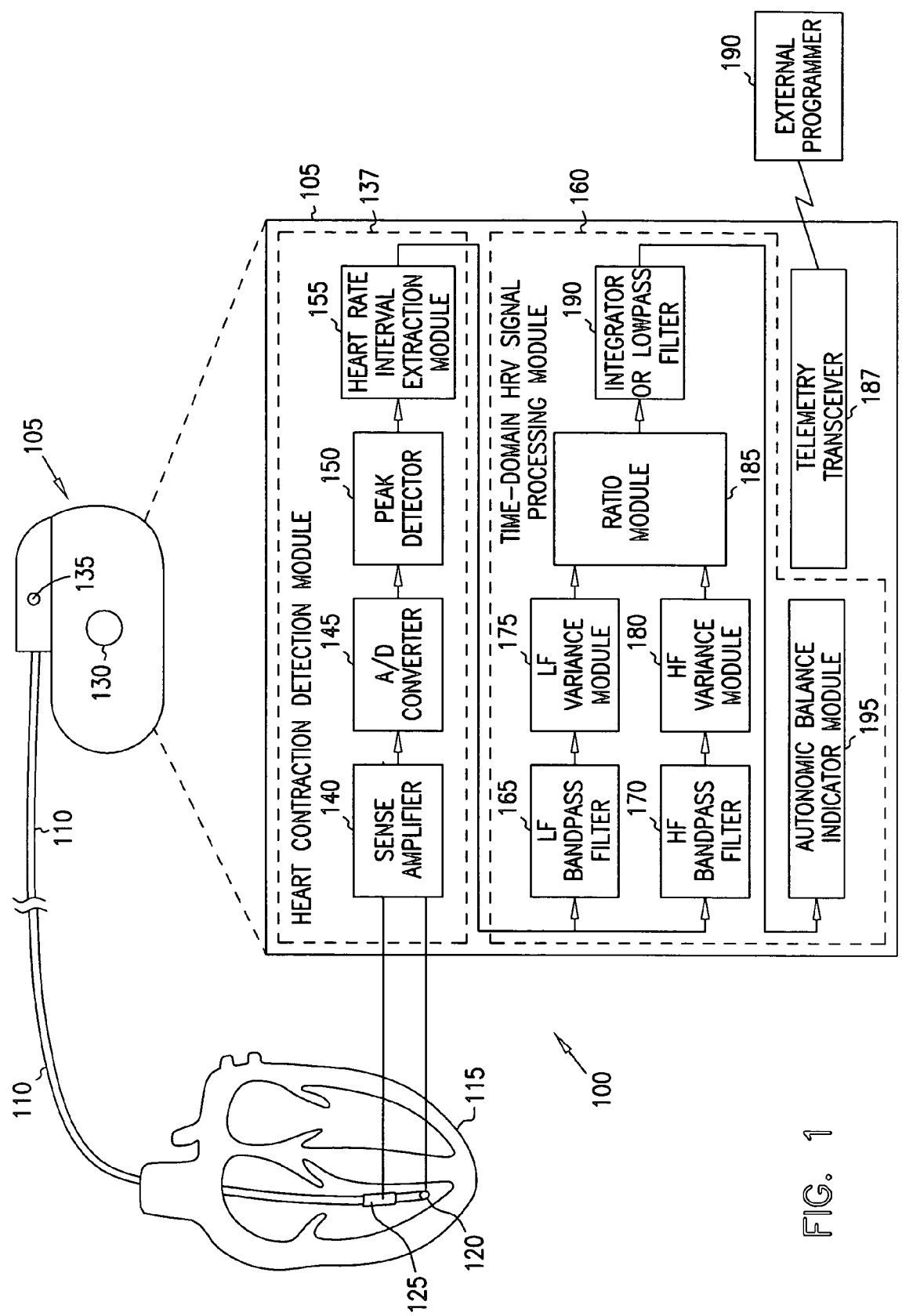
FIG. 1 is a schematic/block diagram illustrating generally one embodiment of portions of a cardiac rhythm management system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

The present methods and apparatus will be described in applications involving implantable medical devices including, but not limited to, implantable cardiac rhythm management systems such as pacemakers, cardioverter/defibrillators, pacer/defibrillators, biventricular or other multi-site coordination devices, and drug delivery systems. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders, whether such devices are used for providing a diagnostic, a therapy, or both a diagnostic and a therapy.

This document describes a cardiac rhythm management system that provides an indication of patient well-being, based on an autonomic balance between the sympathetic and vagal components of the autonomic nervous system, using time-domain processing of frequency components of a heart rate interval signal.

FIG. 1 is a schematic/block diagram illustrating generally one embodiment of portions of a cardiac rhythm management system 100. In this embodiment, system 100 includes, among other things, a cardiac rhythm management device 105 and a leadwire ("lead") 110 for communicating signals between device 105 and a portion of a living organism, such as a heart 115. Embodiments of device 105 include, among other things, bradycardia and antitachycardia pacemakers, cardioverters, defibrillators, combination pacemaker/defibrillators, drug delivery devices, and any other implantable or external cardiac rhythm management apparatus capable of providing therapy and/or diagnostics to heart 115. System 100 may also include additional components such as, for example, a remote programmer 190 capable of communicating with device 105 via a transmitter or receiver, such as telemetry transceiver 187.

In one embodiment, portions of system 100 (e.g., device 105) are implantable in the living organism, such as in a pectoral or abdominal region of a human patient, or elsewhere. In another embodiment, portions of system 100 (e.g., device 105) are alternatively disposed externally to the human patient. In the illustrated embodiment, portions of lead 110 are disposed in the right ventricle, however, any other positioning of lead 110 is included within the present invention. For example, in various alternative embodiments, lead 110 may alternatively be positioned in a location that is associated with the right atrium and/or superior vena cava, the coronary sinus or great cardiac vein, the left atrium or ventricle, epicardially, or elsewhere. In one embodiment, lead 110 is a commercially available bipolar pacing lead having a tip electrode 120 and a ring electrode 125 configured to be disposed in a right ventricle of heart 115. System 100 can also include other leads and/or electrodes in addition to lead 110, appropriately disposed, such as in or around heart 115, or elsewhere. For example, in one external embodiment, device 105 is not implanted and lead 110 provides external surface ECG electrode connections for sensing heart signals. In a unipolar example, implanted device 105 itself includes one or more electrodes for sensing heart signals or providing therapy, such as housing electrode 130 or header electrode 135.

FIG. 1 also illustrates generally portions of device 105, together with schematic illustrations of example connections to the various electrodes. Device 105 includes a heart contraction detection module 137 that receives intrinsic heart signals from electrodes that are communicatively associated with heart 115. Module 137 provides an output heart rate interval signal carrying information about the time intervals between heart contractions. Because, as discussed above, the interval between heart contractions manifests intrinsic variations, the output heart rate interval signal provided by module 137 includes heart rate variability information.

In one embodiment, module 137 includes a sense amplifier 140, which, in this illustration, is coupled to tip electrode 120 and ring electrode 125 for receiving intrinsic heart signals that include electrical depolarizations corresponding to heart contractions (right ventricular heart contractions, in this example). Sense amplifier 140 detects such input heart depolarizations and provides an output electrical signal carrying such information to subsequent portions of device 105. In a further embodiment, sense amplifier 140 also includes filtering or other signal processing circuits for detecting the desired electrical depolarizations associated with heart contractions, as is known in the art. Device 105 also includes an analog-to-digital (A/D) converter 145, which receives the sensed electrical depolarization signal and provides an output digital representation thereof. In a further embodiment, A/D converter 145 includes associated sample and hold circuits for sampling the electrical signal output by sense amplifier 140. Peak detector 150 receives the digitized signal from A/D converter 145 and detects signal peaks associated with heart contractions. In this embodiment, these signal peaks are the R-waves in the QRS complexes associated with ventricular heart contractions. However, it is understood that the disclosed structure and techniques could also be used to detect atrial heart contractions using P-waves associated with atrial depolarizations.

In the illustrated embodiment, peak detector 150 outputs information about the timing of each R-wave to heart interval extraction module 155. Based on this information, heart rate interval extraction module 155 provides a discrete-time signal that is periodically sampled, i.e., the time difference between such samples is uniform. Each such sample includes an associated time interval ("heart rate interval") corresponding to the detected heart rate.

Figure 2:
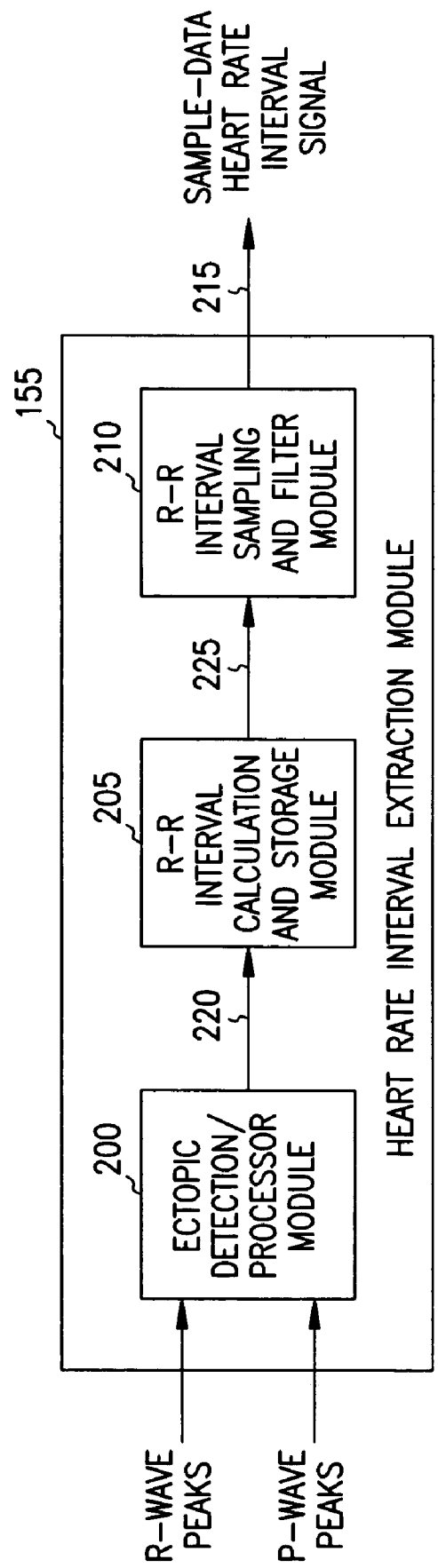
FIG. 2 is a schematic/block diagram illustrating generally one embodiment of portions of a heart rate interval extraction module.

FIG. 2 is a schematic/block diagram, illustrating generally one embodiment of portions of heart rate interval extraction module 155, which includes an ectopic detection/processor module 200, an R—R interval calculation and storage module 205, and an R—R interval sampling and filter module 210. Heart rate interval extraction module 155 outputs a sampled data heart rate interval signal 215 that includes R—R interval information. In FIG. 2, ectopic detection/processor module 200 receives the detected R-wave peaks from peak detector 150. Module 200 deletes, replaces, and/or suppresses from further processing ectopic R-waves (sometimes referred to as premature ventricular contractions, or "PVCs"). Ectopic R-waves do not result from a normal sinus rhythm, that is, from a conducted atrial depolarization.

In one embodiment, ectopic detection/processor module 200 also receives detected P-wave peaks, corresponding to atrial depolarizations, from electrodes associated with an atrium and sensed by an atrial sense amplifier (not shown).

Figure 3:
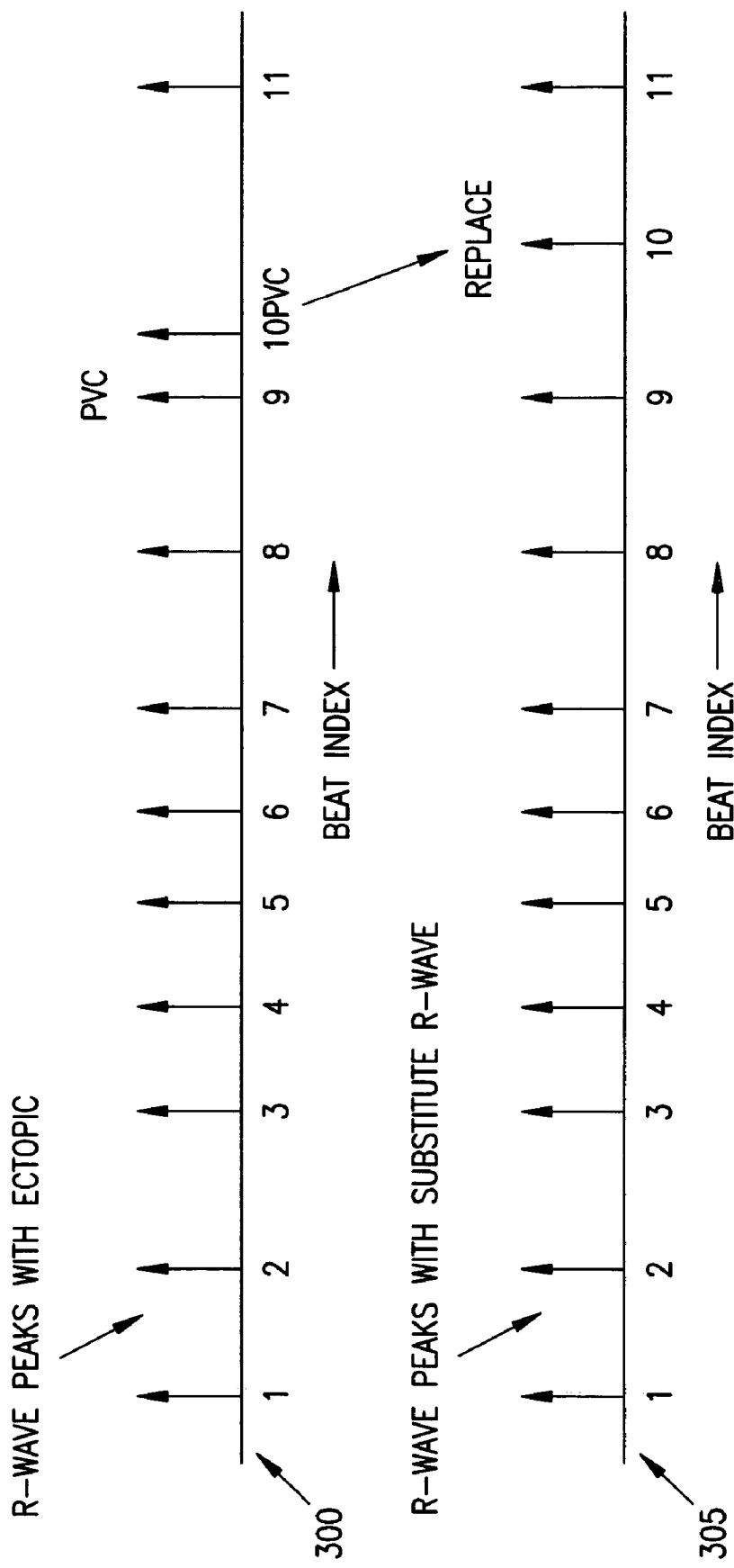
FIG. 3 is a graph illustrating generally one embodiment of a technique for processing a signal that includes R-wave information including providing a substitute R-wave to replace a premature ventricular contraction (PVC) or ectopic beat.

This embodiment of operating ectopic detection/processor module 200 is illustrated generally by the signal graph of FIG. 3. The input signal 300 of FIG. 3 illustrates instances of detected R-wave peaks, depicted by upward arrows. In FIG. 3, any detected R-wave for which no P-wave was detected since the preceding R-wave is deemed a PVC. PVCs are suppressed in output signal 305 from further signal processing. Such PVCs are replaced in output signal 305 by a substitute R-wave at the estimated time at which such R-wave would have occurred had there not been an ectopic event. In FIG. 3, beat number 10 represents a PVC that is replaced by a substitute R-wave.

Many techniques exist for generating a substitute R-wave. In one example, the PVC is replaced by a substitute R-wave placed at time that is interpolated from that of following and preceding nonectopic R-waves. Because PVCs sometimes occur in groups, however, other techniques may also be used. Such techniques include using a moving average-like technique, spline-like technique, or median-like technique. A predetermined number of R—R intervals before and/or after the PVC may be used to calculate a time of occurrence of the substitute R-wave when a PVC occurs.

Figure 4:
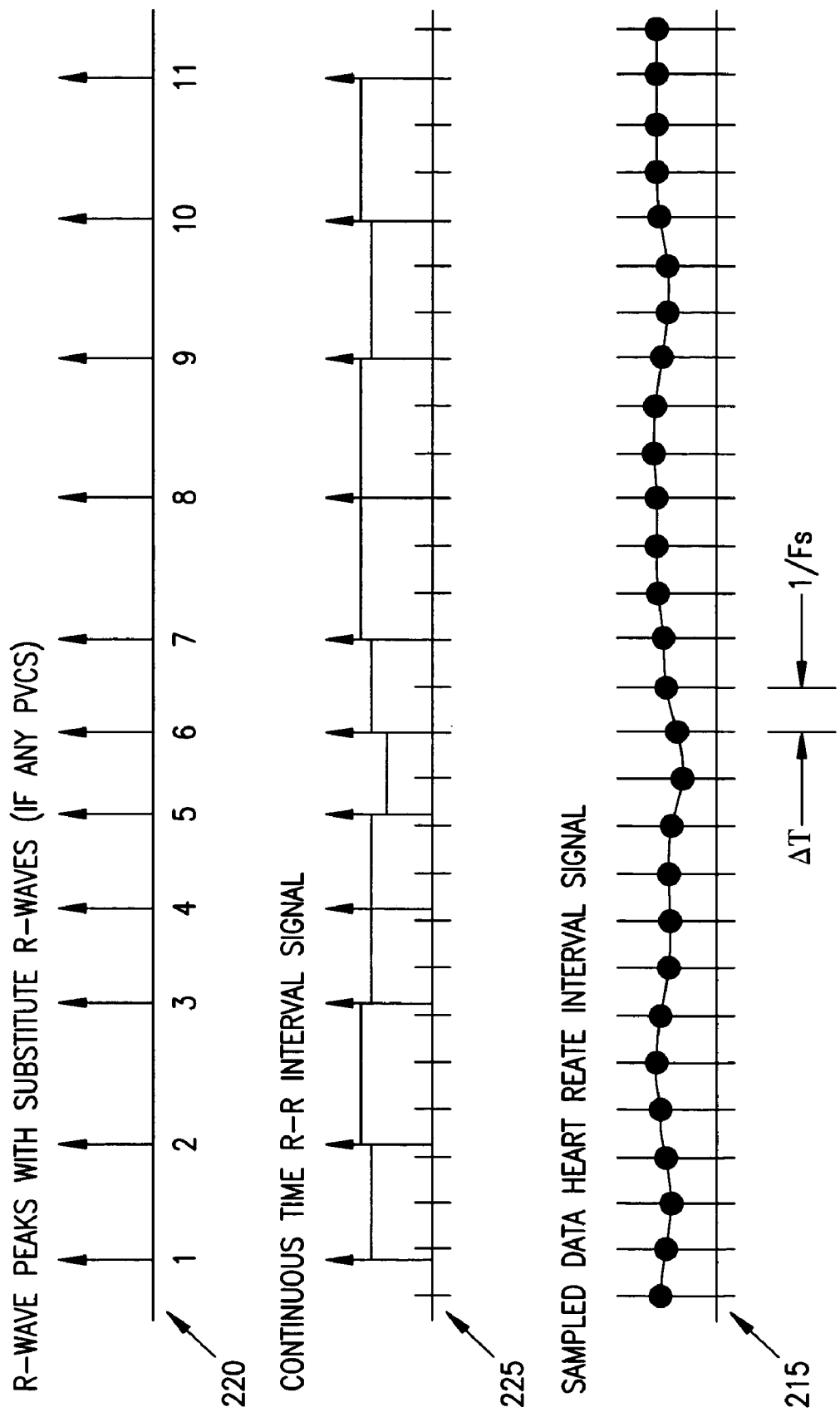
FIG. 4 is a graph illustrating generally one embodiment of a technique for processing a signal that includes R-wave information, including forming a continuous-time R—R interval signal and a sampled data heart rate interval signal that includes R—R interval information.

FIG. 4 is a signal graph illustrating generally one embodiment of the operation of R—R interval calculation and storage module 205 and R—R interval sampling and filter module 210. R—R interval calculation and storage module 205 receives, from ectopic detection/processor module 200, a signal 220 including R-wave peaks with any substituted R-waves. Module 205 includes a timer that determines the R—R time interval between detected R-wave peaks, and stores the R—R intervals in memory to provide a resulting continuous time R—R interval signal 225. Signal 225 is sampled by module 210 to produce the resulting sampled data heart rate interval signal 215, which includes R—R interval information.

In one embodiment, module 210 includes a sampling module that samples signal 225 at a sampling frequency, $f_s$, exceeding the Nyquist criterion. For example, if the maximum expected heart rate (after PVC removal) is 180 beats per minute, then a sampling rate that is greater than or equal to 6 Hz is sufficient. In one embodiment, this sampling module portion of module 210 also includes a finite impulse response (FIR) lowpass filter (or similar lowpass filter, averager, decimator, or downsampler) that provides a smoothed sampled data heart rate interval signal 210.

Figure 5:
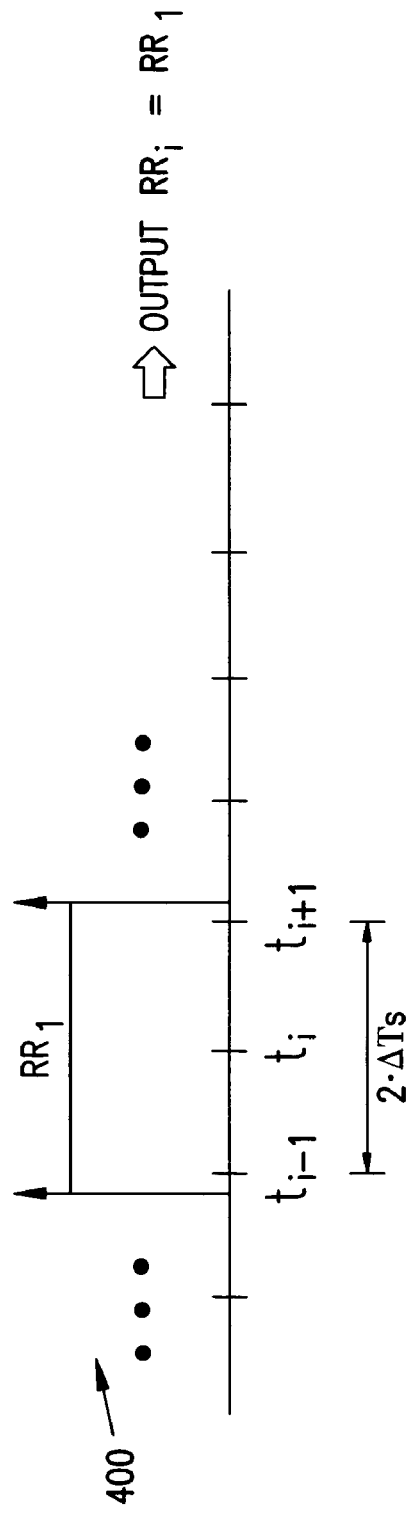
FIG. 5 is a graph illustrating generally one embodiment of a technique for sampling and filtering a continuous-time R—R interval signal to obtain a resulting sampled data heart rate interval signal that includes R—R interval information.
Figure 5:
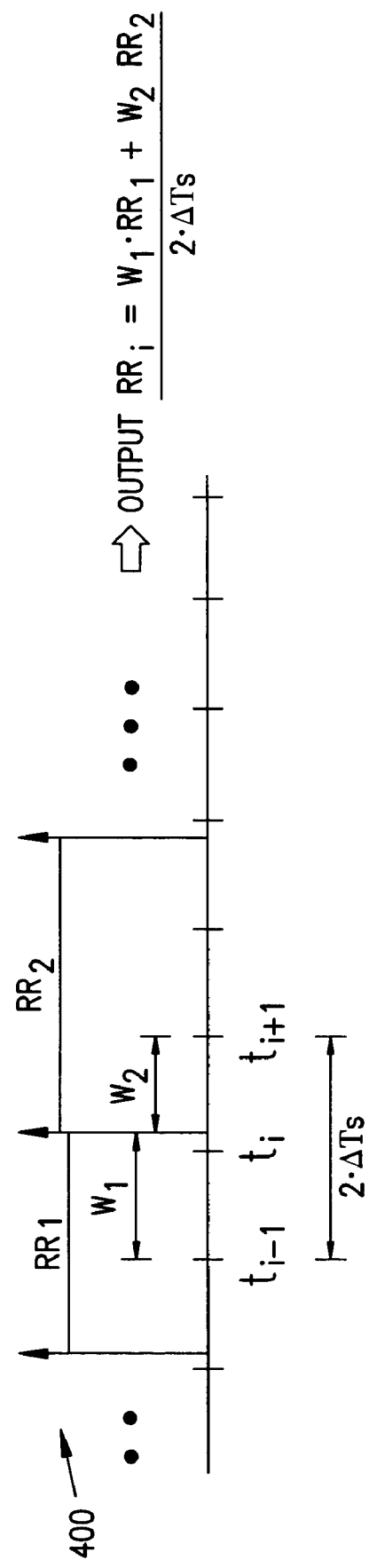

In one embodiment, a three sample point FIR filter is used to sample and filter continuous time R—R interval signal 225. These sample points are separated from each by a time interval, $\Delta T_s$, where $\Delta T_s$ is the inverse of the sampling frequency, $f_s$. In operation, if the three sample points (at times $t=t_{i-1}$, $t_i$, and $t_{i+1}$) fall within the same R—R interval of continuous time R—R interval signal 225, then that R—R interval value is used as the corresponding output sample, $RR_i$. Otherwise, if the three sample points span a pair of R—R intervals (i.e., first and second R—R intervals, $RR_1$ and $RR_2$) on continuous time R—R interval signal 225, a weighted average of the first and second R—R interval values is used as the corresponding output sample, $RR_i$. Each of the first and second R—R interval values is weighted according to the fraction of the time, $(t_{i+1}-t_{i-1})$ associated with that one of the first and second R—R intervals, $RR_1$ and $RR_2$. Operation of such a filter is illustrated generally by FIG. 5.

FIG. 1 also illustrates a time-domain heart rate variability (HRV) signal processing module 160 that receives the heart rate interval signal 215 from heart rate interval extraction module 155, and provides a resulting indicator of patient well-being. In one embodiment of HRV signal processing module 160, the input heart rate interval signal 215 is received by a low frequency (LF) bandpass filter 165 and by a high frequency (HF) bandpass filter 170. In one embodiment, LF bandpass filter 165 is a finite impulse response (FIR) type filter having a lowpass cutoff frequency that is approximately equal to 0.15 Hz, and a highpass cutoff frequency that is approximately equal to 0.04 Hz. As a result, LF bandpass filter 165 outputs a filtered heart rate interval signal having frequency components that are primarily approximately between 0.04 Hz and 0.15 Hz inclusive. In this embodiment, HF bandpass filter 170 is an FIR type filter having a lowpass cutoff frequency that is approximately equal to 0.40 Hz, and a highpass cutoff frequency that is approximately equal to 0.15 Hz. As a result, HF bandpass filter 170 outputs a filtered heart rate interval signal having frequency components approximately between 0.15 Hz and 0.40 Hz inclusive. Appropriate infinite impulse response (IIR) filter structures could also be used. Since the ultimate measurement of patient well-being is based on variance, waveform distortion is not of great concern and, therefore, the filter need not provide linear phase.

LF variance module 175 and HF variance module 180 receive the output signals from LF bandpass filter 165 and HF bandpass filter 170, respectively. These variance modules 175 and 180 each perform a variance-type or similar computation, respectively outputting LF variance and HF variance signals to ratio module 185. In one embodiment, variance modules 175 and 180 each include a squaring circuit (i.e., a circuit that multiplies the input by itself to provide an output signal that is equivalent to the input signal raised to the second power) followed by a lowpass filter (or integrator or averager) to provide the resulting output signal. This squaring and lowpass filtering operation is equivalent to a variance computation that provides an indication of heart rate variability within the associated frequency range. In one embodiment, the lowpass filter used by variance modules 175 and 180 is an IIR type filter having a single lowpass pole with exponential weighting of past samples occurring during a moving time window that is approximately between 2 and 5 minutes, inclusive, in length.

Ratio module 185 receives the LF and HF variance output signals from LF variance module 175 and HF variance module 180, respectively, and divides the value of the LF variance by the HF variance. The resulting LF/HF ratio output by ratio module 185 provides an indication of the sympathovagal balance between the sympathetic and parasympathetic/vagal components of the autonomic nervous system. As discussed above, an increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. In one embodiment, this LF/HF ratio output by ratio module 185 is itself used as a patient wellness indicator. In further embodiments, however, this LF/HF ratio signal undergoes further processing, as discussed below.

For example, in one such further embodiment, the LF/HF ratio signal output by ratio module 185 is received by a lowpass filter (or integrator or averager) 190 to provide additional smoothing of the indication of patient well-being. In one such example, lowpass filter 190 is implemented as an exponential-weighted averager (i.e., more recent samples are weighted more than older samples) over a sliding time window that is approximately between 2 minutes and 5 minutes inclusive, such as about 5 minutes. The resulting smoothed LF/HF ratio signal output by lowpass filter 190 provides a more stable indication of the patient's sympathovagal balance; one such smoothed LF/HF ratio signal is illustrated generally, by way of example, but not by way of limitation, in the graph of FIG. 3, together with a corresponding sample heart rate interval signal on which the smoothed LF/HF ratio is based.

Figure 6:
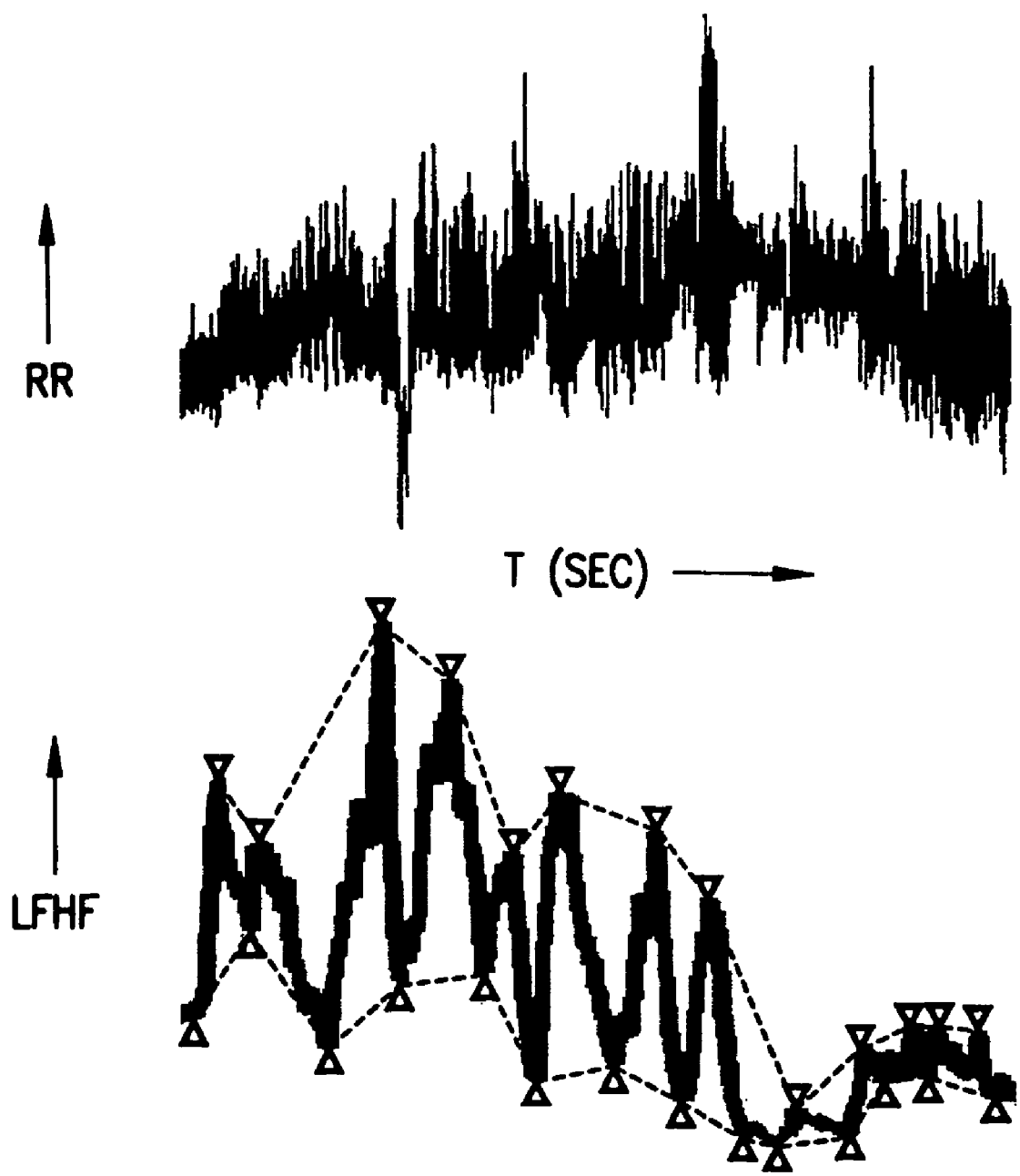
FIG. 6 is a graph illustrating generally one embodiment of a LF/HF signal representing autonomic balance based on an illustrated corresponding heart (e.g., R—R) interval signal, and illustrating generally one embodiment of a technique for extracting one or more features of the LF/HF signal to further quantify a state of the patient's well-being.

In a still further embodiment, the smoothed LF/HF ratio signal is received by autonomic balance indicator module 195 for further processing. In one example, module 195 includes a peak detector for obtaining the local minima and/or maxima of the smoothed LF/HF ratio signal, as illustrated in FIG. 6. Thus, in one embodiment, the indication of autonomic balance is based on one or more features of the smoothed LF/HF ratio signal, such as the local minima (e.g., using the lowest local minima during a given time period, an average of the local minima during a given time period, etc.), the local maxima, slope of the smoothed LF/HF ratio signal, and/or slope of portions of the LF/HF envelope (e.g., lines drawn between successive local minima and lines drawn between successive local maxima). In a further embodiment, the desired indication of autonomic balance is communicate by telemetry transceiver 187 to external programmer 190, such as for processing and/or for visual, audible, or other diagnostic display to the physician or other user.

Figure 7:
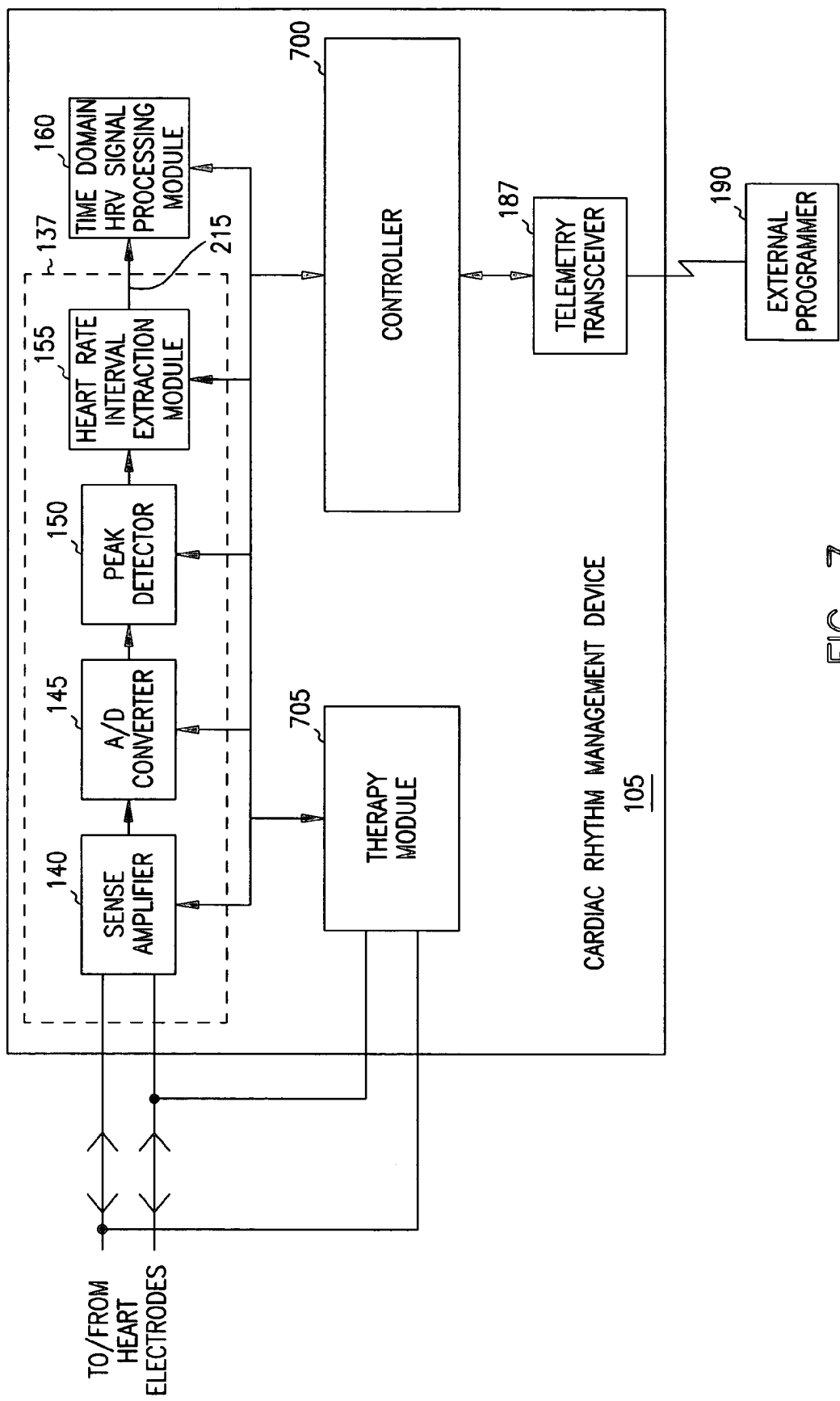
FIG. 7 is a schematic/block diagram illustrating generally one embodiment of portions of a cardiac rhythm management device including a therapy module providing therapy based at least in part on the indication of autonomic balance.

FIG. 7 is a schematic/block diagram illustrating generally, by way of example, and not by way of limitation, one embodiment of portions of device 105 including a controller 700 and a therapy module 705. Therapy module 705 provides cardiac rhythm management therapy to heart 115 via electrodes that are communicatively associated therewith. Examples of such therapy include, without limitation, atrial or ventricular pacing therapy, antitachyarrhythmia therapy, multi-site coordination therapy such as biventricular pacing, drug delivery. In one such embodiment, the parameters of such therapy are adjusted and/or optimized by controller 700 based at least in part on one or more indications of sympathetic/parasympathetic balance obtained from time-domain HRV signal processing module 160. For example, such parameters for providing dual chamber pacing therapy are well known in the art (e.g., rate, amplitude, pulsewidth, AV-delay, etc.); such parameters are adjusted, either individually or in combination, to increase or decrease a particular indication of autonomic balance (e.g., to decrease the lowest local minima of the smoothed LF/HF signal). Such parameter optimization is performed either in device 105 or, alternatively, in external programmer 190.

In another example, the real-time (i.e., not substantially delayed) indicator of sympathetic/vagal balance provided by module 160 alerts the device to time periods during which heart 115 is particularly susceptible to tachyarrhythmias, such as when the smoothed or unsmoothed LF/HF signal increases (e.g., beyond a threshold value or at a rate that exceeds a threshold rate). In this embodiment, the increase in the LF/HF indication predicts the likely present or future onset of a tachyarrhythmia and, as a result, controller 700 triggers the delivery of preventative antitachyarrhythmia therapy to prevent the occurrence of the tachyarrhythmias. Such antitachyarrhythmia therapy includes antitachyarrhythmia pacing (ATP) sequences and/or antiarrhythmic drug therapy using drugs that increase parasympathetic and/or decrease sympathetic activity. Thus, this embodiment provides real-time control of therapy delivery based on the then-existing (or slightly delayed) indication of sympathetic/vagal balance.

Figure 8:
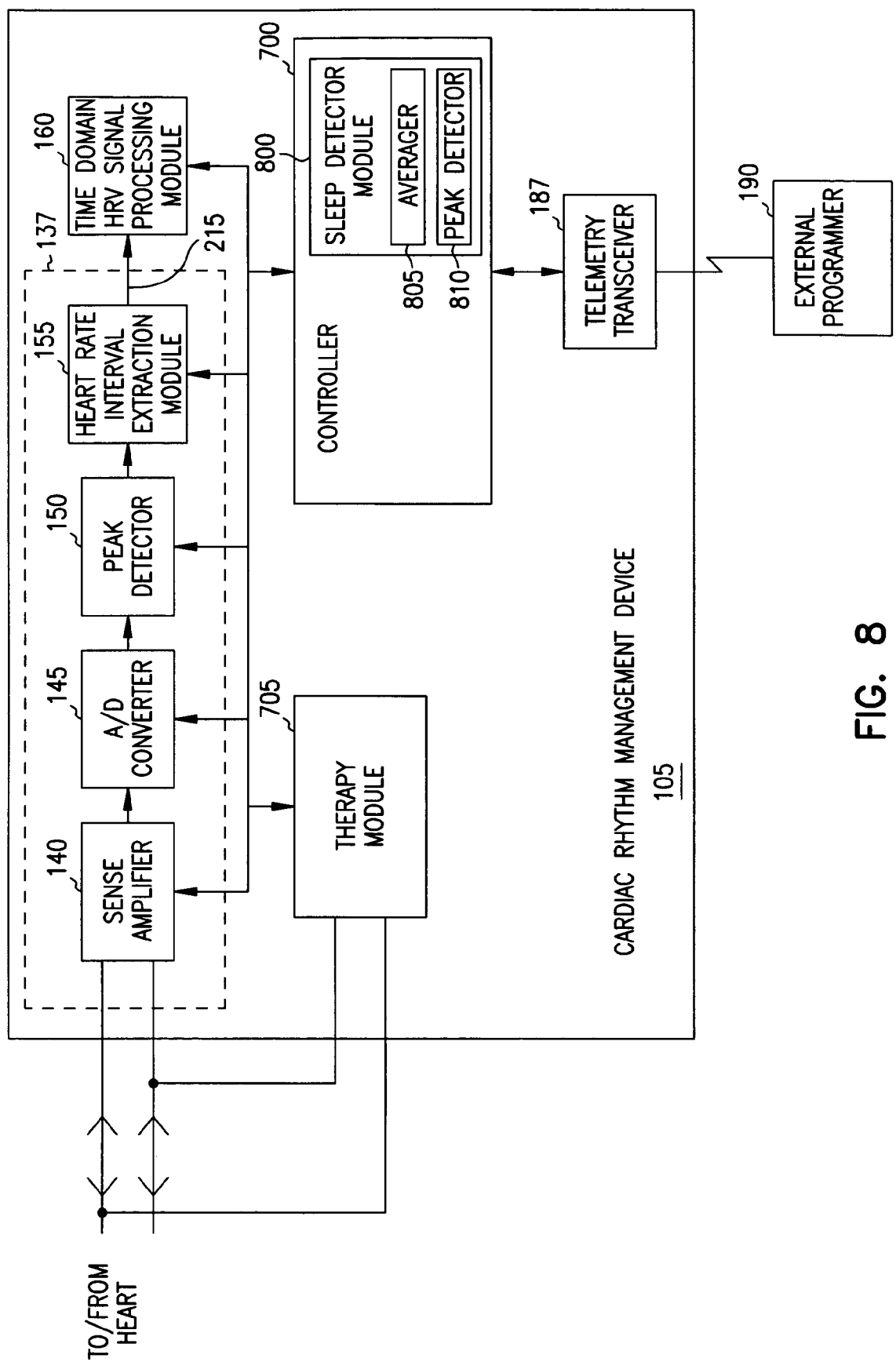
FIG. 8 is a schematic/block diagram illustrating generally one embodiment of portions of a cardiac rhythm management system including a means (such as a "sleep" detector) for identifying one or more particular time periods of interest for obtaining the indication of autonomic balance.
Figure 9:
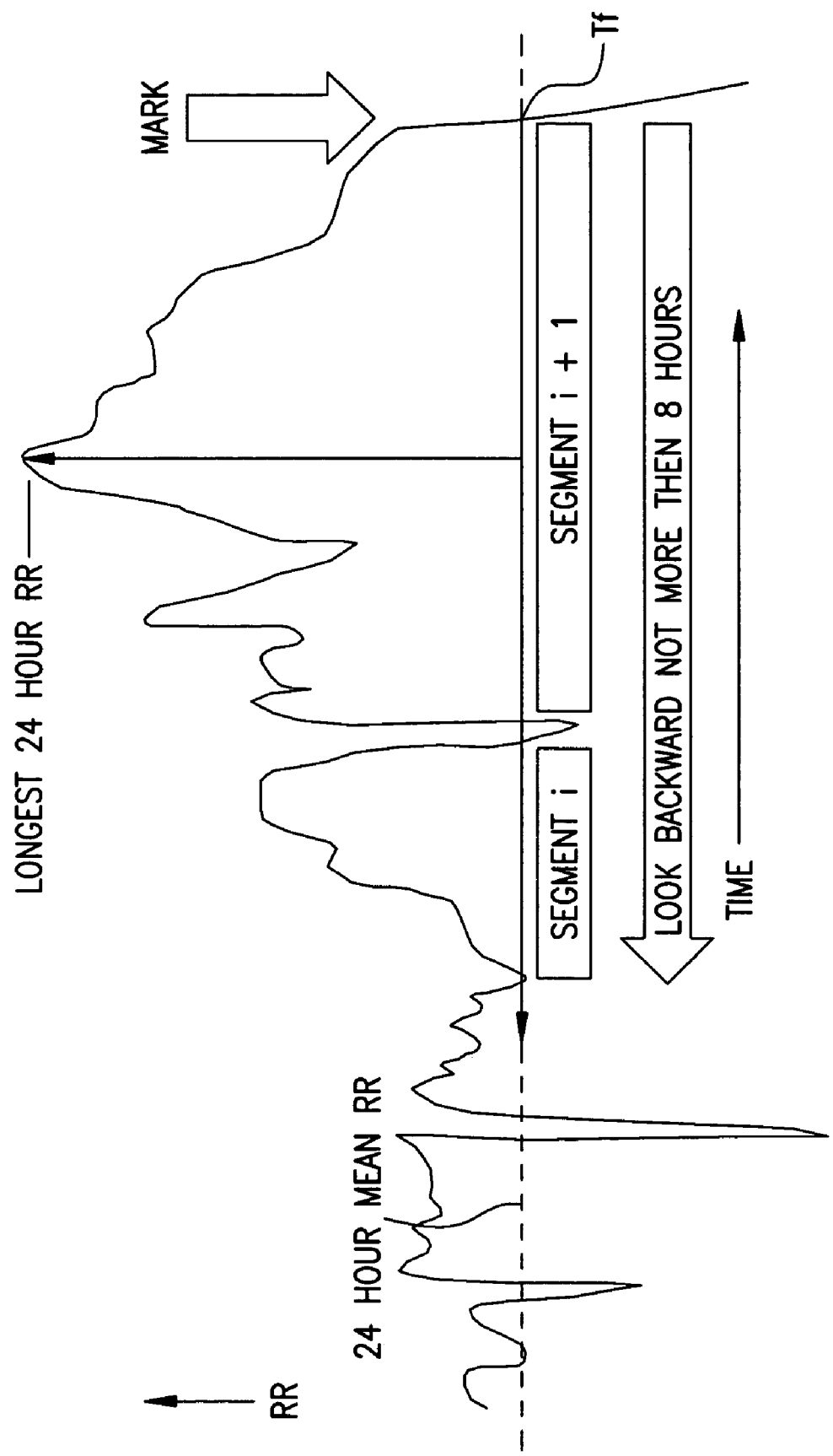
FIG. 9 is a graph illustrating generally one technique for identifying a time period of interest for determining autonomic balance, in which the time period of interest is based on data regarding the intervals between heart contractions.

FIG. 8 is a schematic/block diagram illustrating generally, by way of example, but not by way of limitation one embodiment of portions of device 105 in which controller 700 (or, alternatively, external programmer 190) includes a "sleep detector" module 800 or other similar module for identifying, one or more particular time periods of interest for obtaining the indication of synpathetic/vagal balance. In one embodiment, sleep detector 800 includes a long term (e.g., 24 hour) averager 805 for storing the long term average interval between heart contractions (e.g., R—R interval), and a long term (e.g., 24 hour) peak detector 810 for storing a corresponding long term maximum interval between heart contractions (e.g., maximum R—R interval). In this embodiment, autonomic balance indicator module 195 of FIG. 1 provides an indication of patient well-being based on sympathetic/vagal balance as obtained only when the interval between heart contractions exceeds the long term average value over a time period that: (1) extends forward in time from the time corresponding to the maximum interval between heart contractions to the first time, $T_f$, at which the interval between heart contractions drops back to the long term average value: and (2) extends backward in time from the time corresponding to the maximum interval between heart contractions to a time that is not more than 8 hours (by way of example) earlier than the time $T_f$. Intervals during this time period in which the interval between heart contractions is less than the long term average value are, in one embodiment, ignored for the purposes of providing an indication of sympathetic/parasympathetic balance. This described technique is illustrated generally, by way of example, but not by way of limitation, in FIG. 9. This technique is particularly useful for ascertaining longer term (e.g., over a period of days or months) variations in the patient's well-being as determined from sympathetic/parasympathetic balance. Because exercise, posture, and even being awake affect the sympathetic/parasympathetic balance, these factors are de-emphasized for ascertaining such longer term variations in the patient's well-being. While the time periods used in such techniques may be deemed "sleep," as referred to in this document by the use of the term "sleep detector module," it is understood that such times may not correspond exactly to periods during which the patient is sleeping. Other suitable time periods may also be used to de-emphasize components of the patient's sympathetic/vagal balance that tend to confound an assessment of long-term well-being.

CONCLUSION

This document describes, among other things, a cardiac rhythm management system that provides an indication of patient well-being based on the autonomic balance between the sympathetic and vagal components of the autonomic nervous system, using time-domain processing of frequency components of a heart rate interval signal. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled.

In the appended claims, the terms "including" and "in which" are used as plain-English equivalents of the respective terms "comprising" and "wherein."

What is claimed is:

1. A method including:
   detecting ventricular heart contractions over a time period;
   detecting atrial heart contractions over the time period;
   if any ventricular heart contraction is not preceded by a corresponding atrial contraction, then deeming that ventricular heart contraction a premature ventricular contraction (PVC);
   replacing the PVC with a substitute R-wave at that time which the R-wave would have occurred had the PVC not occurred;
   obtaining a time-domain first signal representing time intervals between the detected ventricular heart contractions, wherein the detected ventricular heart contractions include any substitute R-waves generated as a result of a PVC;
   filtering the first signal to obtain a time-domain second signal including frequency components substantially in a first frequency band, wherein the second signal is influenced by both sympathetic and parasympathetic components of an autonomic nervous system;
   filtering the first signal to obtain a time-domain third signal including frequency components substantially in a second frequency band, wherein the third signal is influenced by the parasympathetic component of the autonomic nervous system and not substantially influenced by the sympathetic component of the autonomic nervous system;
   obtaining a time domain variance of each of the second and third signals; and
   providing an indication associated with a balance between the sympathetic and parasympathetic components of the autonomic nervous system based on a ratio between the time-domain variances of the second and third signals.

2. The method of claim 1, in which the replacing the PVC with a substitute R-wave includes interpolating a time of the substitute R-wave from a most recent nonectopic ventricular contraction and an earliest subsequent nonectopic ventricular contraction.

3. The method of claim 1, in which the replacing the PVC with a substitute R-wave includes computing a time of the substitute R-wave using a moving average.

4. The method of claim 1, in which the replacing the PVC with a substitute R-wave includes using a spline to compute a time of the substitute R-wave.

5. The method of claim 1, in which the replacing the PVC with a substitute R-wave includes using a median to compute a time of the substitute R-wave.

6. The method of claim 1, in which the replacing the PVC with a substitute R-wave includes using a number of RR intervals before the PVC to compute a time of the substitute R-wave.

7. The method of claim 1, in which the replacing the PVC with a substitute R-wave includes using a number of RR intervals after the PVC to compute a time of the substitute R-wave.

8. The method of claim 1, wherein obtaining the variance comprises:
   squaring each of the second and third signals; and
   lowpass filtering each squared second and third signals.

9. The method of claim 1, further including lowpass filtering the ratioed variance of the second and third signals.

10. The method of claim 1, in which providing an indication associated with an autonomic nervous system includes extracting a signal feature of the ratioed variance of the second and third signals.

11. A method including:
    detecting heart contractions over a time period;
    obtaining a time-domain first signal representing time intervals between the detected heart contractions;
    filtering the first signal to obtain a time-domain second signal including frequency components substantially in a first frequency band, wherein the second signal is influenced by both sympathetic and parasympathetic components of an autonomic nervous system;
    filtering the first signal to obtain a time-domain third signal including frequency components substantially in a second frequency band, wherein the third signal is influenced by the parasympathetic component of the autonomic nervous system and not substantially influenced by the sympathetic component of the autonomic nervous system;
    obtaining a time domain variance of each of the second and third signals;
    providing a balance indication associated with a balance between the sympathetic and parasympathetic components of the autonomic nervous system based on a ratio between the time-domain variances of the second and third signals; and
    automatically adjusting a therapy at least in part by using the balance indication to control the adjusting.

12. The method of claim 11, in which the adjusting the therapy includes using a present value of the balance indication.

13. The method of claim 11, in which the adjusting the therapy includes using a delayed value of the balance indication.

14. The method of claim 11, in which the adjusting the therapy includes selecting at least one therapy parameter value so as to increase a value of the balance indication.

15. The method of claim 11, in which the adjusting the therapy includes selecting at least one therapy parameter value so as to decrease a value of the balance indication.

16. The method of claim 11, in which the balance indication is an LF/HF signal, and in which adjusting the therapy includes delivering a preventative antitachyarrhythmia therapy when a value of the balance indication exceeds a threshold value.

17. The method of claim 11, in which the adjusting the therapy includes using the balance indication to control the adjusting in real-time.

18. A method including:
    detecting heart contractions over a time period;
    obtaining a time-domain first signal representing time intervals between the detected heart contractions;
    filtering the first signal to obtain a time-domain second signal including frequency components substantially in a first frequency band, wherein the second signal is influenced by both sympathetic and parasympathetic components of an autonomic nervous system;
    filtering the first signal to obtain a time-domain third signal including frequency components substantially in a second frequency band, wherein the third signal is influenced by the parasympathetic component of the autonomic nervous system and not substantially influenced by the sympathetic component of the autonomic nervous system;
    obtaining a time domain variance of each of the second and third signals; and providing an indication associated with a balance between the sympathetic and parasympathetic components of the autonomic nervous system based on a ratio between the time-domain variances of the second and third signals during a period of time that is deemed to correspond to a resting state.

19. The method of claim 18, in which during the period of time an interval between adjacent heart contractions generally exceeds a long-term average value.

20. The method of claim 19, in which the period of time includes a first interval that extends forward from a first time corresponding to a maximum interval between adjacent heart contractions to a second time when the interval between adjacent heart contractions first drops back to the long-term average value.

21. The method of claim 20, in which the period of time includes a second interval that extends backward in time from a third time corresponding to a maximum interval between adjacent heart contractions to a fourth time that is not more than a fixed time amount earlier than the third time.

22. The method of claim 19, in which the period of time includes a second interval that extends backward in time from a first time corresponding to a maximum interval between adjacent heart contractions to a second time that is not more than a fixed time amount earlier than the first time.

* * * * *